US008121679B2

(12) United States Patent
Fruitman

(10) Patent No.: US 8,121,679 B2
(45) Date of Patent: Feb. 21, 2012

(54) TRANSCUTANEOUS ELECTRICAL NERVE STIMULATOR WITH HOT OR COLD THERMAL APPLICATION

(76) Inventor: Clinton O. Fruitman, Chandler, AZ (US)

( * ) Notice: Subject to any disclaimer, the term of this patent is extended or adjusted under 35 U.S.C. 154(b) by 627 days.

(21) Appl. No.: 11/025,615

(22) Filed: Dec. 29, 2004

(65) Prior Publication Data

US 2006/0142816 A1 Jun. 29, 2006

(51) Int. Cl.
*A61N 1/04* (2006.01)
(52) U.S. Cl. .............. 607/3; 607/46; 607/48; 607/115; 607/149; 607/153
(58) Field of Classification Search .............. 607/62, 607/46, 48, 115, 3, 149, 153; 60/62, 46, 60/48, 115, 3, 149, 153
See application file for complete search history.

(56) References Cited

U.S. PATENT DOCUMENTS

| 4,462,224 | A | | 7/1984 | Dunshee et al. |
| 4,676,246 | A | | 6/1987 | Korenaga et al. |
| 4,867,166 | A | * | 9/1989 | Axelgaard et al. ............ 600/391 |
| 5,009,228 | A | * | 4/1991 | Clark .............................. 607/46 |
| 5,097,828 | A | | 3/1992 | Deutsch |
| 5,281,287 | A | * | 1/1994 | Lloyd et al. ..................... 156/80 |
| 5,314,423 | A | | 5/1994 | Seney |
| 5,336,255 | A | * | 8/1994 | Kanare et al. ................. 607/149 |
| 5,601,618 | A | * | 2/1997 | James ............................. 607/71 |
| 5,824,033 | A | | 10/1998 | Ferrari et al. |
| 2002/0107543 | A1 | | 8/2002 | Voznesensky et al. |
| 2003/0225356 | A1 | | 12/2003 | Kulichikhin et al. |
| 2004/0138712 | A1 | | 7/2004 | Tamarkin et al. |

* cited by examiner

*Primary Examiner* — Niketa Patel
*Assistant Examiner* — Joseph Stoklosa
(74) *Attorney, Agent, or Firm* — Zeman-Mullen & Ford, LLP

(57) ABSTRACT

A Transcutaneous Electrical Nerve Stimulator (TENS) and electrode pad that is capable simultaneously of delivering hot or cold thermal therapy for the relief of pain.

8 Claims, 7 Drawing Sheets

TRANSCUTANEOUS ELECTRICAL NERVE STIMULATOR WITH HOT OR COLD THERMAL APPLICATION

FIELD OF INVENTION

This invention relates, generally, to a method and apparatus for electro-stimulation with simultaneous cold or heat therapy. More particularly, the present invention relates to a transcutaneous nerve stimulator having at least two opposing electrodes contained within a housing or a high thermal mass polymer matrix. If the electrodes are contained within a housing, the device also includes a thermal reservoir contained within the housing.

BACKGROUND OF THE INVENTION

Transcutaneous Electrical Nerve Stimulation (TENS) technology is a well known and accepted method of treating pain whereby a very low current electrical signal (e.g., 1 to 150 Hz, 30 to 250 micro second pulse width, and voltages typically less than 400 V DC) is passed through the skin with conductive electrodes. There are three likely theories as to the mechanism of action:
  A. Gating Theory—electrical stimuli generated by a TENS device excites sensory nerve pathways to the point where they become chemically fatigued and cease to send pain signals to the brain.
  B. Endorphin Theory—a physiological response to the irritation produced by electrical stimuli is pain induced endorphin release.
  C. Physiological Change Theory—the pulsed signal of a TENS stimulation can cause localized muscle activity leading to increased circulation in the treated areas and removal of metabolic toxins.

Traditional heat therapy may predate mankind as even animals are known to soak themselves in hot springs. Heat usually feels good because of the increased circulation it generates in affected tissue. This increased circulation relieves pain by improving tissue oxygenation thus removing metabolic toxins. The disadvantage of heat therapy is that it can aggravate an inflammatory response.

Cold therapy is less often chosen by individuals for pain treatment because of the discomfort of ice on the skin. However, it is widely recognized as a powerful treatment for many types of pain by physicians and therapists and is often used for acute injuries. This therapy has two known mechanisms of action:
  A. Although initially uncomfortable, cold contact is a heat sink that acts as a powerful anti-inflammatory by rapidly drawing heat out of affected tissue.
  B. Cold temperatures have an anesthetic and numbing effect on sensory nerves.

The drawback to cold therapy is that prolonged application, and excessively reduced temperature can cause decreased blood supply producing shivering and muscle tension.

The combined effects of thermal therapy and TENS therapy are disclosed in U.S. Pat. Nos. 5,097,828, 5,314,423 and 5,336,255. U.S. Pat. No. 5,314,423 describes a pain alleviating tissue treatment assembly that uses a combination of a cold electrode and an alterable current source to reduce the temperature of a selected tissue area while simultaneously applying various selected reversing and/or non-reversing currents to the selected tissue. This patent teaches that electrode chilling allows nerve stimulation enhancement with significantly greater energy input while not increasing patient discomfort.

U.S. Pat. No. 5,336,255 teaches an electrical stimulation heat/cool pack pouch made from waterproof lined fabric connected by loop and hook devices (Velcro) to conductive fabric patch electrodes backed with a wire lead. This device has built in insulating air gaps (Velcro) between the electrodes and the heat sink/reservoir such that the heat transfer is minimized at the electrode sites.

U.S. Pat. No. 5,097,828 discloses a therapeutic device for heating or cooling the skin that includes a handle, a thermally conductive head secured to the handle, and a thermally conductive member secured to the front end of the head. A thermoelectric means heats or cools the thermally conductive member and the head includes a thermally conductive portion adjoining the thermoelectric means such that the head can function as a heat sink.

Both hot and cold packs can be uncomfortable and sometimes damaging to tissue depending on temperature, contact time of the thermal reservoir, and thermal conductivity of the containment material. In tests for the present invention, applied heat has been determined to be less effective with TENS therapy than applied cold with TENS therapy.

Drawbacks do exist with prior art. U.S. Pat. Nos. 5,314,423 and 5,097,828 teach actively chilled electrodes and contact devices, however, these methods are impractical for portable use as they require support devices such as fluid chillers in one case, and in the case of Peltier chilled electrodes, cumbersome power supplies and heat exchanger devices. In addition, the chilling attachments to the electrodes can be awkward for mobile TENS application. Further, with respect to U.S. Pat. No. 5,336,255, cloth on wire type TENS electrode patches are usually fragile. When they inadvertently separate from the skin, the electrical discharge from the reduced contact area can sting and even burn the skin. In addition, electrically conductive rubber patches (usually carbon filled silicone) often have high electrical resistance of about 20 k$\Omega$ through a 1 mm thickness.

Electrode patch adhesives used in the prior art also share drawbacks. First, electrode patch adhesives can pull hair on removal from the skin and these adhesives are sometimes difficult to clean. Second, as the skin sweats, the adhesives may lose some of their grip and develop a change in electrical conductivity related to fluid absorption in the adhesive. Finally, adhesives dry out causing changes in stiction and conductivity. TENS electrodes and adhesives are typically such poor thermal conductors, that if one tries to combine an ice bag placement over a set of electrode patches, the treated area will have warm spots at the electrode sites.

SUMMARY OF THE INVENTION

In general, the present invention provides a TENS device that is simultaneously capable of delivering hot or cold thermal therapy. In one exemplary embodiment of the invention, a soft, solid, oil gel elastomer, filled with high thermal mass particles is cast or injected over and around at least two opposing electrodes of similar polymer filled with conductive carbon.

In another exemplary embodiment of the present invention, a stiff elastomer is mixed with high thermal mass particles and then formed as a hollow case or housing with walls, a lid, and a base surrounding at least two opposing electrodes. After the housing is formed, the cavity is filled with a gel that can be either frozen or heated such as, for example, a gel comprising polyacrylamide, water, and potassium chloride. After filling with a gel, the cavity is then sealed.

In still another exemplary embodiment of the present invention, the hollow housing formed above may be formed with a re-sealable lid through which a chemical cold or hot pack, or other heat reservoir, can be placed after activating them.

BRIEF DESCRIPTION OF THE DRAWINGS

The present invention will hereinafter be described in conjunction with the appended drawing figures, wherein like numerals denote like elements, and.

DETAILED DESCRIPTION OF THE EXEMPLARY EMBODIMENTS

The present invention is directed to a transcutaneous electrical nerve stimulator (TENS) that is capable of simultaneously delivering hot or cold thermal therapy for pain relief. The device includes electrodes and a thermal reservoir body that are contained within the same housing or medium which comprises the device. The electrodes typically have relatively low resistivity—i.e. under 2 kΩ/mm thickness and the thermal reservoir has a high thermal mass.

The electrodes and the non-electrode regions of the device have similar thermal conductivity to enable somewhat uniform heat transfer and similar mechanical properties to minimize separation stresses. The device possesses adequate thermal conductivity for effective heat transport but low enough thermal conductivity to minimize discomfort and damage if the device should inadvertently be chilled below recommended therapeutic limits.

The electrodes are permanently fixed and therefore incapable of curling away from the skin thereby reducing the risk of a stress concentrating electrical discharge. The electrode assembly of the device is easily aligned with the pain site by the patient themselves. In one exemplary embodiment, the device comprises a soft, gel like texture for comfort and easy conformation to body parts.

The device is compact in size to facilitate easy handling and placement and an electronic signal generator can be embedded in the device to eliminate lead issues such as tangling and safety. Finally, the device is simple to operate and can be controlled remotely.

Construction

Figure 1:
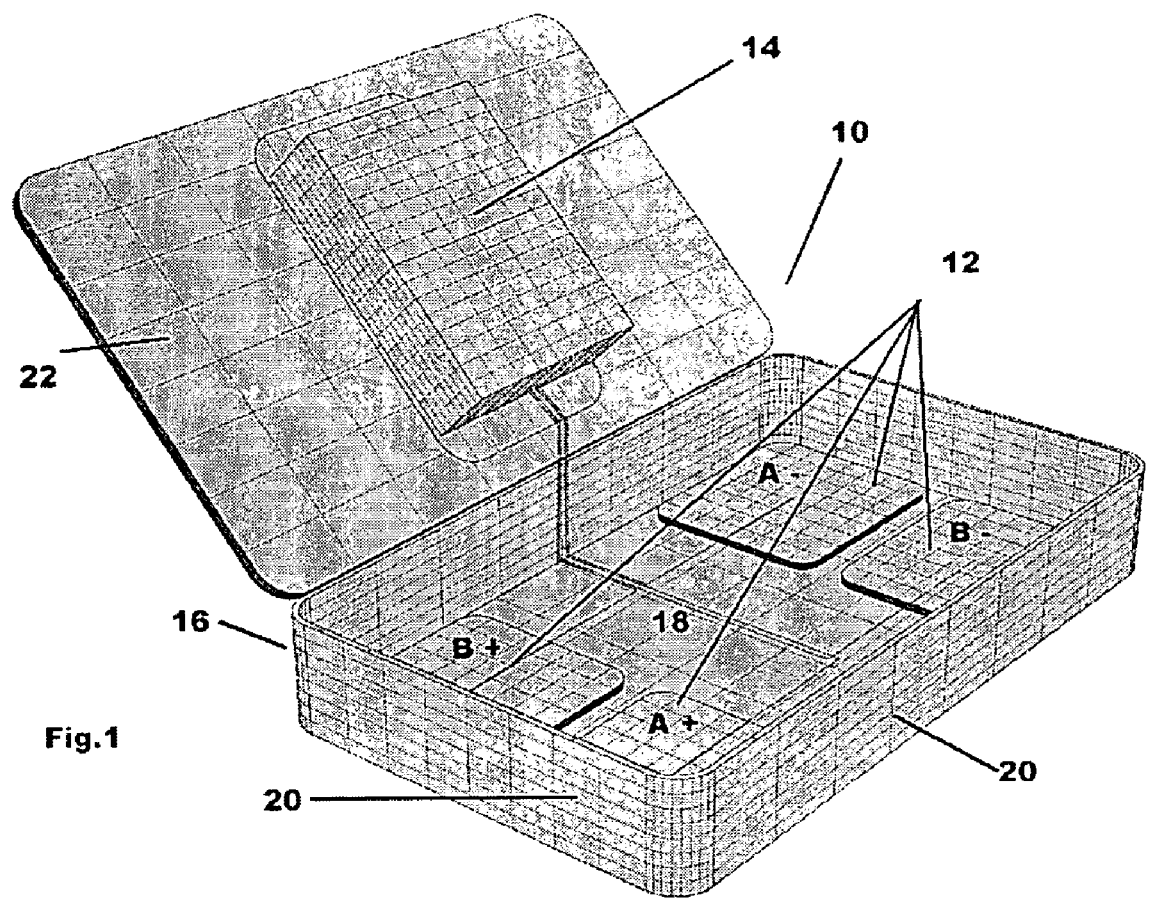
FIG. 1 is an open, top perspective view of one exemplary embodiment of the device of the present invention.

FIG. 1 shows a perspective view of one exemplary embodiment of the device 10 of the present invention which includes at least one pair of opposing electrodes 12 and a signal generating power supply 14, a hollow space for a thermal reservoir contained within the housing 16 or other medium such as a soft gel elastomer. As shown in FIG. 1, the housing 16 may comprise a hollow case with a base 18, sidewalls 20 and a lid 22 wherein the lid may be resealable. As with typical TENS devices, this invention uses either two opposed pole electrodes or four diagonally opposed electrodes (FIG. 1) and delivers a very low current, pulsed signal of up to 150 Hz and up to 400 V DC.

Figure 2:
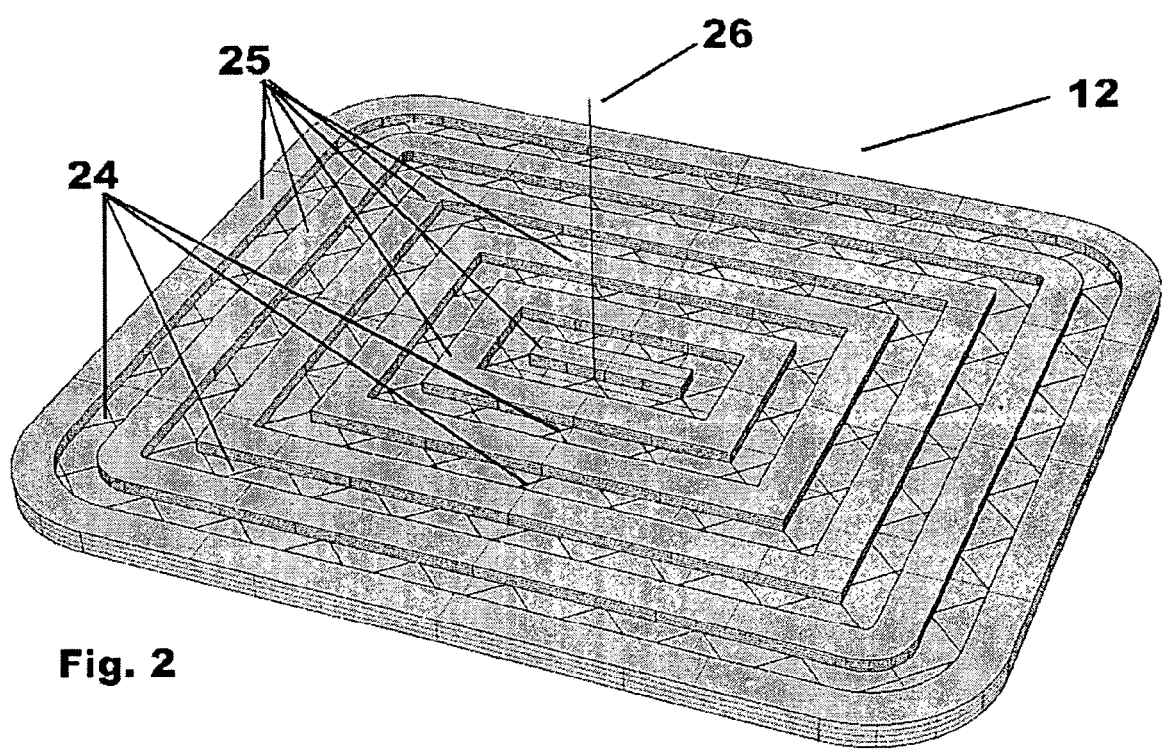
FIG. 2 is a perspective view of one of the diagonally opposed electrodes shown in FIG. 1.

A perspective view of an opposing electrode 12 shown in FIG. 1 is depicted in FIG. 2. Opposing electrode 12 may be fabricated from any combination of either conductive mats 24, metal wires 24 or foils 24 impregnated and covered with elastomers 25 that have been filled with dispersed particles of conductive metals, carbon black (2 to 25%) or inherently conductive polymers (ICPs). To enhance thermal mass and thermal conductivity, the electrodes can also be filled with metal oxide particles. The elastomers include the classes of materials comprising Urethanes, Silicones, Acrylics, Hydrogels, Polyolefins, Synthetic Rubbers, Natural Rubbers and Oil Gels. In one preferred embodiment, the elastomer is a very soft mineral oil plasticized styrenated rubber (SEBS). In this embodiment, the thermal reservoir is composed of a SEBS (Kraton G1652) dissolved into mineral oils with 50% wt. of alumina powder (Fujimi PWA 9) dispersed into the mix. The electrode in this particular preferred embodiment is composed of perforated copper foil impregnated and coated with a mixture of mineral oil plus a Maleated SEBS rubber (Kraton FG1901X) and filled with 4% to 10% highly conductive carbon filler (AKZO Nobel Ketjenblack EC600). Also in this preferred embodiment, an electrical wire 26 is attached to one of a conductive mat, a metal coil, a metal screen, or an expanded perforated metal foil which is embedded in the conductive elastomer.

Figure 3:
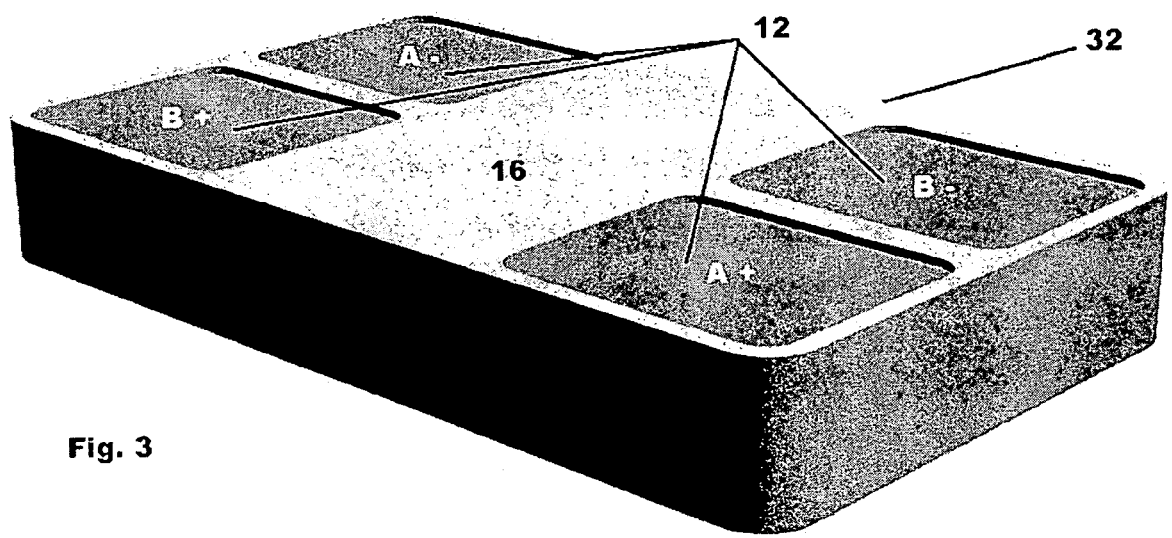
FIG. 3 is a bottom perspective view of one exemplary embodiment of the device of the present invention.
Figure 4:
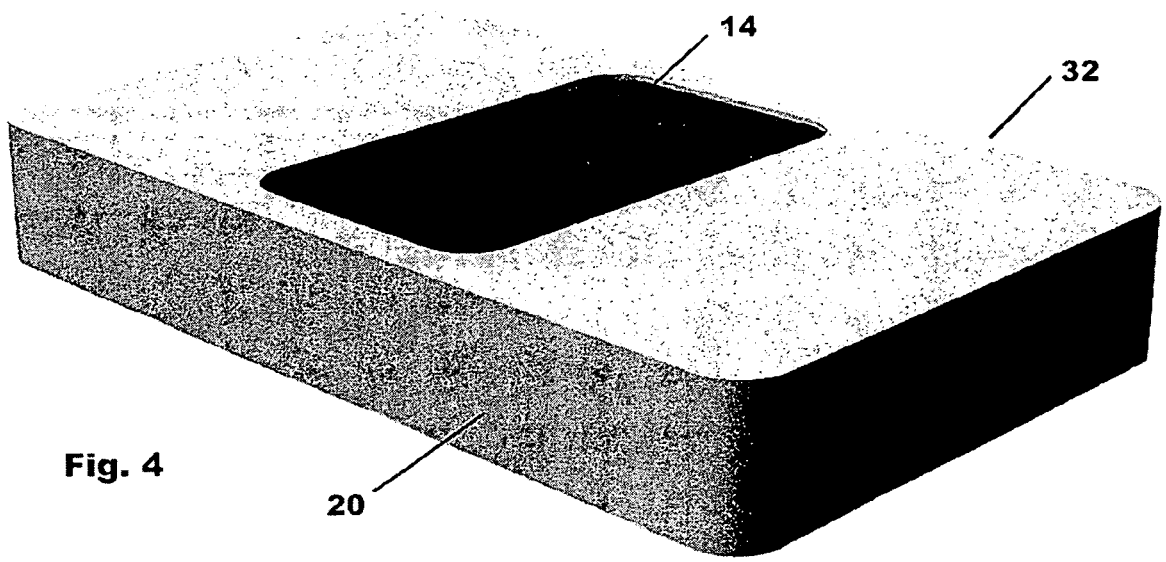
FIG. 4 is a closed, top perspective view of the exemplary embodiment of the device shown in FIG. 1.

FIGS. 3 and 4 show bottom and top perspective views, respectively, of another exemplary embodiment of the device 32 of the present invention containing a housing 16 which comprises a solid thermal reservoir body or heat sink fabricated from a very soft solid elastomer from one of the above previously identified classes, e.g., mineral oil/SEBS filled with high thermal mass particles such as 50% wt. Aluminum Oxide (Fujimi PWA 9). The material of the thermal reservoir is cast or injected embedding the electrodes 12 and the signal generating power supply 14.

Figure 5:
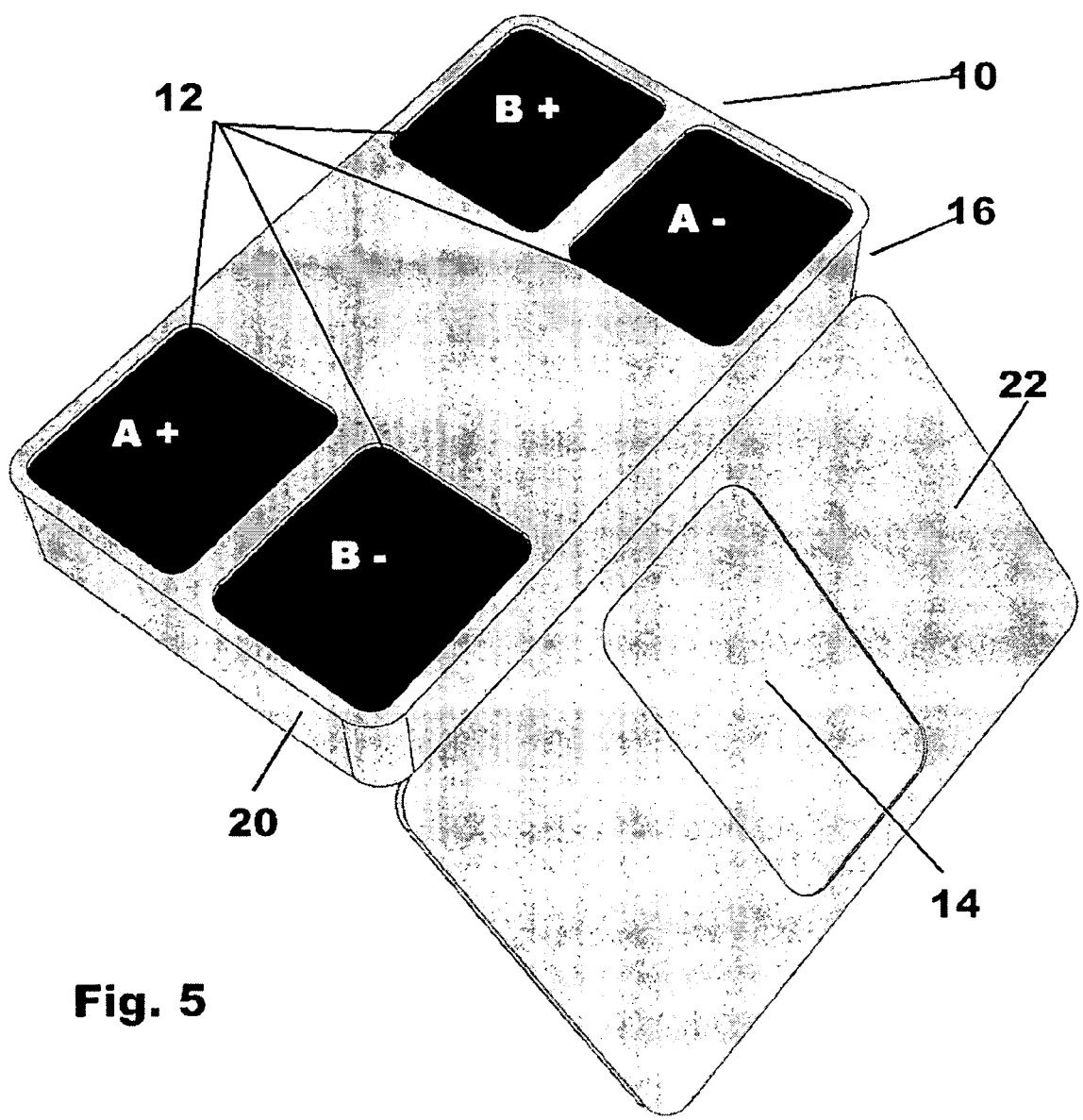
FIG. 5 is an open, bottom perspective view of the exemplary embodiment of the device shown open in FIG. 1.

The thermal reservoir or heat sink and the electrodes may be fabricated in other ways depending on the particular embodiment of the device. However all are effective embodiments. For example, stiffer elastomers from the classes listed above can be mixed with metals or metal oxides as described above and formed as a hollow case with walls, a lid and a base surrounding the electrodes as shown in FIGS. 1, 2 and 5. After forming, the cavity is filled with a freezable or heat-able gel such as a polyacrylimide/water/KCl mixture and sealed.

Figure 7:
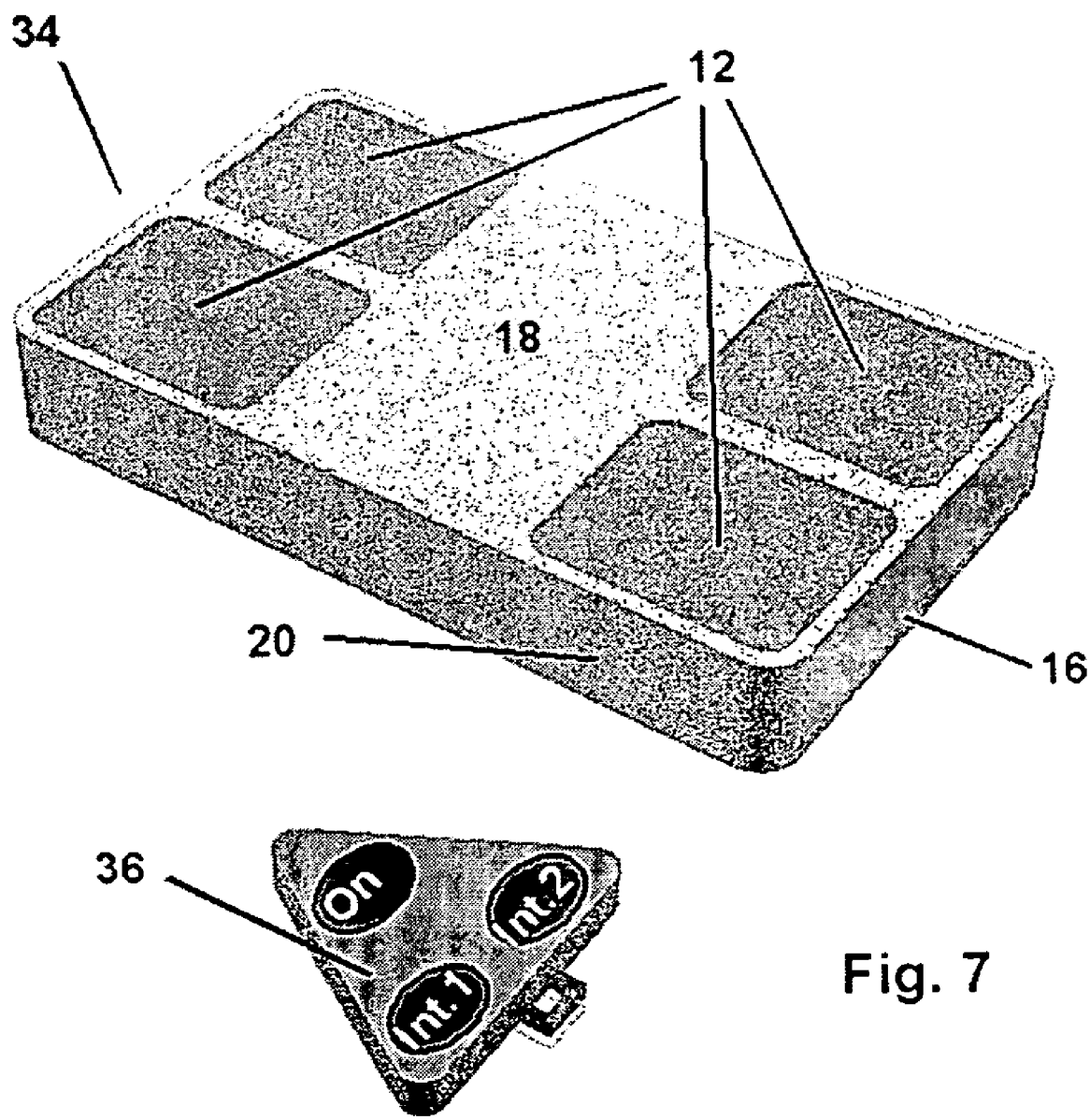
FIG. 7 is a bottom perspective view of yet another exemplary embodiment of the device of the present invention along with a top perspective view of a remote control for the power supply and signal generator that are embedded in the heat reservoir shown in FIGS. 1 and 4.

In still another preferred embodiment of the device 34, a power supply and signal generator are typically embedded in the heat reservoir as shown in FIG. 7 and operated with a separate remote control 36.

Figure 6:
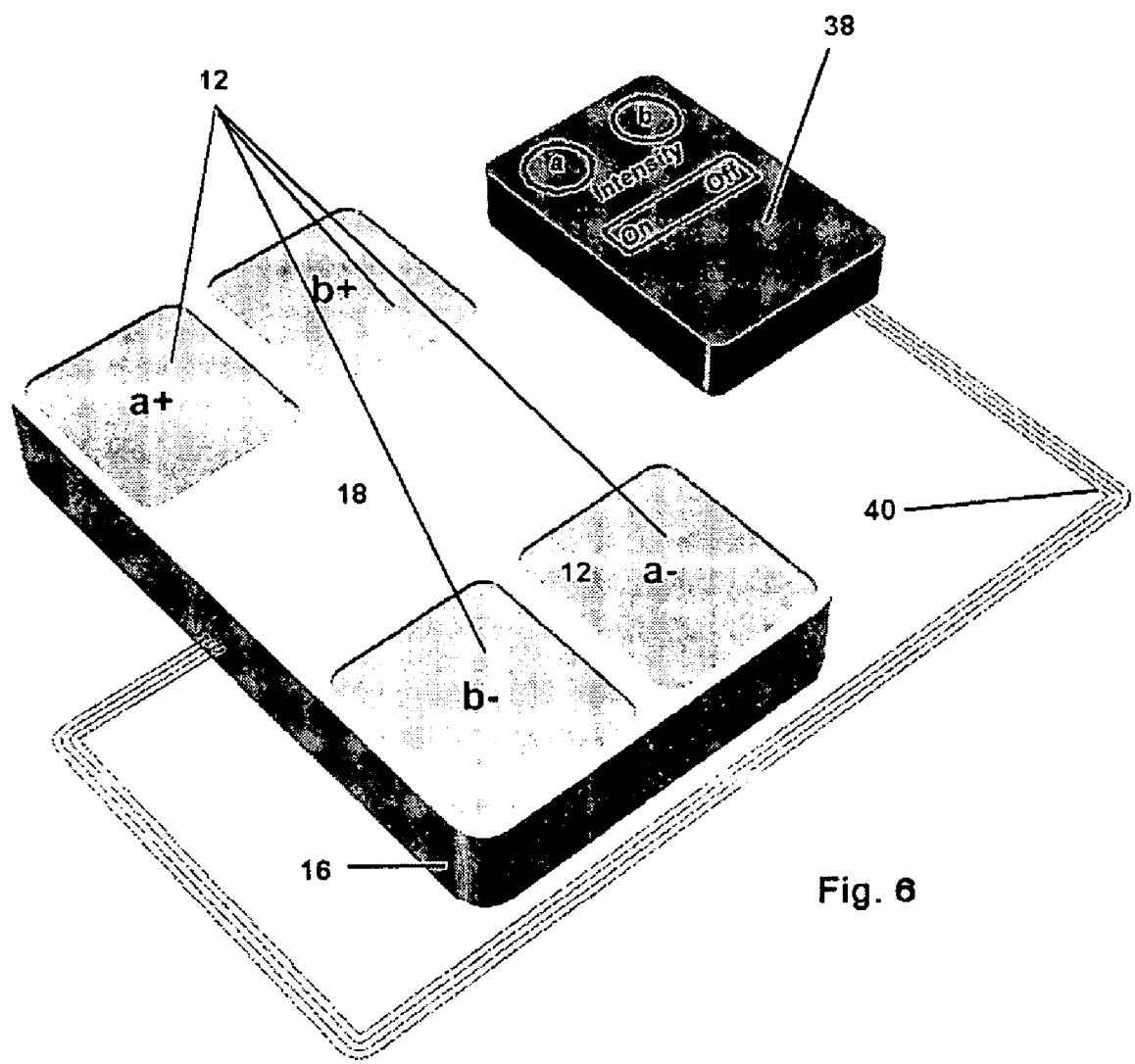
FIG. 6 is a bottom perspective view of still another exemplary embodiment of the device of the present invention along with a top perspective view of the power supply and signal generator attached with an external lead through the reservoir to the electrodes.

In yet another exemplary embodiment the power supply, signal generator and controls 38 are attached with an external lead 40 through the reservoir to the electrodes 12 as shown in FIG. 6.

Application

The assembly can be attached to a desired body part by hand holding, conductive adhesive bonding or strapping and is intended for direct contact with the skin. The device is best activated by chilling to 32 degrees F. with a freezer, a chemical cold pack or other method. If conductive adhesives are not used, a conductive gel or conductive hydrogel (preferred embodiment) is placed in the electrode pockets and the device is mounted to the body directly over a painful area or over a root nerve ascending from the affected area. Non-conductive adhesive may be applied to the non-electrode skin side surface of the device body with conductive gel in the electrode pockets or the device may be held to the body with straps, elastic wrapping or other means.

The device is energized with an appropriate frequency (up to 150 Hz), peak dwell time (bandwidth between 30 μs and 260 μs), intensity (voltage typically less than 150 v) and mode (continuous, burst or varying). These settings are determined experimentally for specific pain regions and can be programmed on either permanent or removable flash memory, PROM or EPROM chips for specific pain targeting sites.

Developmental Results

This device has been very effective relieving various types of neuromuscular and skeletal pain.

In applying the cold body of the device to the skin there is sometimes a very brief discomfort after which a soothing heat transfer takes place and has continued for nearly 30 minutes. Typically a therapeutic effect is seen within five minutes.

In the preferred embodiment where the thermal reservoir and skin contacting material are filled oil gel rubbers, the thermal transfer rate is slow enough that very cold contact is easily tolerated.

With TENS therapy, when the electrical energy is applied, a typical patient adjustment is to increase the intensity until a maximum tolerable surface pain threshold is achieved and then to back off the intensity to a more comfortable level and maintain stimulation until pain relief is achieved. However, unlike conventional TENS therapy, patient testing has shown that combined with cold therapy, maximum tolerable TENS stimulation is not necessary. In fact low levels of stimulation can be very effective.

The patient testing with this device has demonstrated that 15 minute treatments of neuro, muscular and skeletal pain of differing degrees, in various parts of the body typically relieve pain for 2 to 4 hours and in some cases maximum pain levels do not recur until 8 or more hours have passed.

One familiar with the art will realize that this device can be fabricated in many different shapes, sizes, contours and with various numbers of electrodes, e.g. a cervical collar with upper back pad and electrodes or a contoured shoulder, arm or knee system.

The invention claimed is:

1. A transcutaneous electrical nerve stimulator device comprising:
   a housing comprised of a solid thermal reservoir body fabricated from a soft solid polymer which comprises a polymer filled with high thermal mass particles;
   a signal generating power supply embedded within the housing; and
   at least two opposing electrodes embedded within the housing with at least a portion of said electrodes exposed through an outer surface of said housing such that they are capable of contacting a user's skin.

2. The device of claim 1 wherein the soft solid polymer is an oil gel.

3. The device of claim 1 wherein the soft solid polymer comprises an elastomer and the high thermal mass particles comprise metal oxide fillers.

4. The device of claim 1 wherein the soft solid polymer comprises an elastomer and the high thermal mass particles comprise metal fillers.

5. The device of claim 1 wherein circuitry for control inputs, power, and signal outputs is embedded in the housing.

6. The device of claim 5 wherein the control inputs are operated by external remote circuitry.

7. The device of claim 1 wherein external circuitry is used for control inputs and signal generation.

8. The device of claim 1 further comprising an external lead connected to the opposing electrodes.

* * * * *